United States Patent [19]

Ledley

[11] Patent Number: 4,929,832
[45] Date of Patent: May 29, 1990

[54] METHODS AND APPARATUS FOR DETERMINING DISTRIBUTIONS OF RADIOACTIVE MATERIALS

[76] Inventor: Robert S. Ledley, 1002 LaGrande Rd., Silver Spring, Md. 20903

[21] Appl. No.: 291,393

[22] Filed: Dec. 27, 1988

Related U.S. Application Data

[63] Continuation of Ser. No. 170,042, Mar. 11, 1988, abandoned, which is a continuation of Ser. No. 797,725, Nov. 13, 1985, abandoned.

[51] Int. Cl.$^5$ .................................................. G01T 1/00
[52] U.S. Cl. ..................................................... 250/328
[58] Field of Search ........................ 250/328; 378/20, 57

[56] References Cited

U.S. PATENT DOCUMENTS

| | | | |
|---|---|---|---|
| 3,027,453 | 3/1962 | Carter et al. | 455/294 |
| 3,033,986 | 5/1962 | Fowler et al. | 250/328 |
| 3,308,438 | 3/1967 | Spergel et al. | 250/366 |
| 3,793,520 | 2/1974 | Grenier | 378/149 |
| 3,814,939 | 6/1974 | Parker et al. | 250/373 |
| 4,001,591 | 1/1977 | Inbar | 378/149 |
| 4,019,057 | 4/1977 | Bram | 250/375 |
| 4,028,549 | 6/1977 | Baba | 250/336.1 |
| 4,110,615 | 8/1978 | McCann | 250/328 |
| 4,118,632 | 10/1978 | Luig | 378/149 |
| 4,214,161 | 7/1980 | Talroze et al. | 250/364 |
| 4,267,451 | 5/1981 | Berick | 250/367 |
| 4,275,300 | 6/1981 | Abbott | 250/304 |
| 4,298,796 | 11/1981 | Warner et al. | 250/328 |
| 4,311,908 | 1/1982 | Gonlianos et al. | 250/374 |
| 4,431,921 | 2/1984 | Filthuth | 250/374 |
| 4,469,601 | 9/1984 | Beaver et al. | 210/658 |
| 4,582,993 | 4/1986 | Bhattacharya et al. | 250/359.1 |
| 4,598,202 | 7/1986 | It'oechner | 250/366 |
| 4,626,684 | 12/1986 | Landa | 250/328 |

FOREIGN PATENT DOCUMENTS

| | | | |
|---|---|---|---|
| 1939464 | 8/1968 | Fed. Rep. of Germany | 250/328 |
| 1616007 | 3/1971 | Fed. Rep. of Germany | 250/363 S |

Primary Examiner—Janice A. Howell
Assistant Examiner—John C. Freeman
Attorney, Agent, or Firm—Perman & Green

[57] ABSTRACT

A method for determining the distribution of a radioactive material in a medium is provided which comprises the steps of: (a) providing a plurality of radiation detectors at a set of predetermined locations, each of said detectors producing an electrical output indicative of the amount of radioactive material in the vicinity of the detector; (b) moving the medium containing the radioactive material and the plurality of radiation detectors relative to one another so as to position the medium relative to the detectors at each of a set of predetermined positions; and (c) recording the electrical output of each of the detectors at each of the predetermined positions. Apparatus for practicing the method is also provided.

9 Claims, 11 Drawing Sheets

BLOCK DIAGRAM COUNTER/MULTIPLEXER CARD

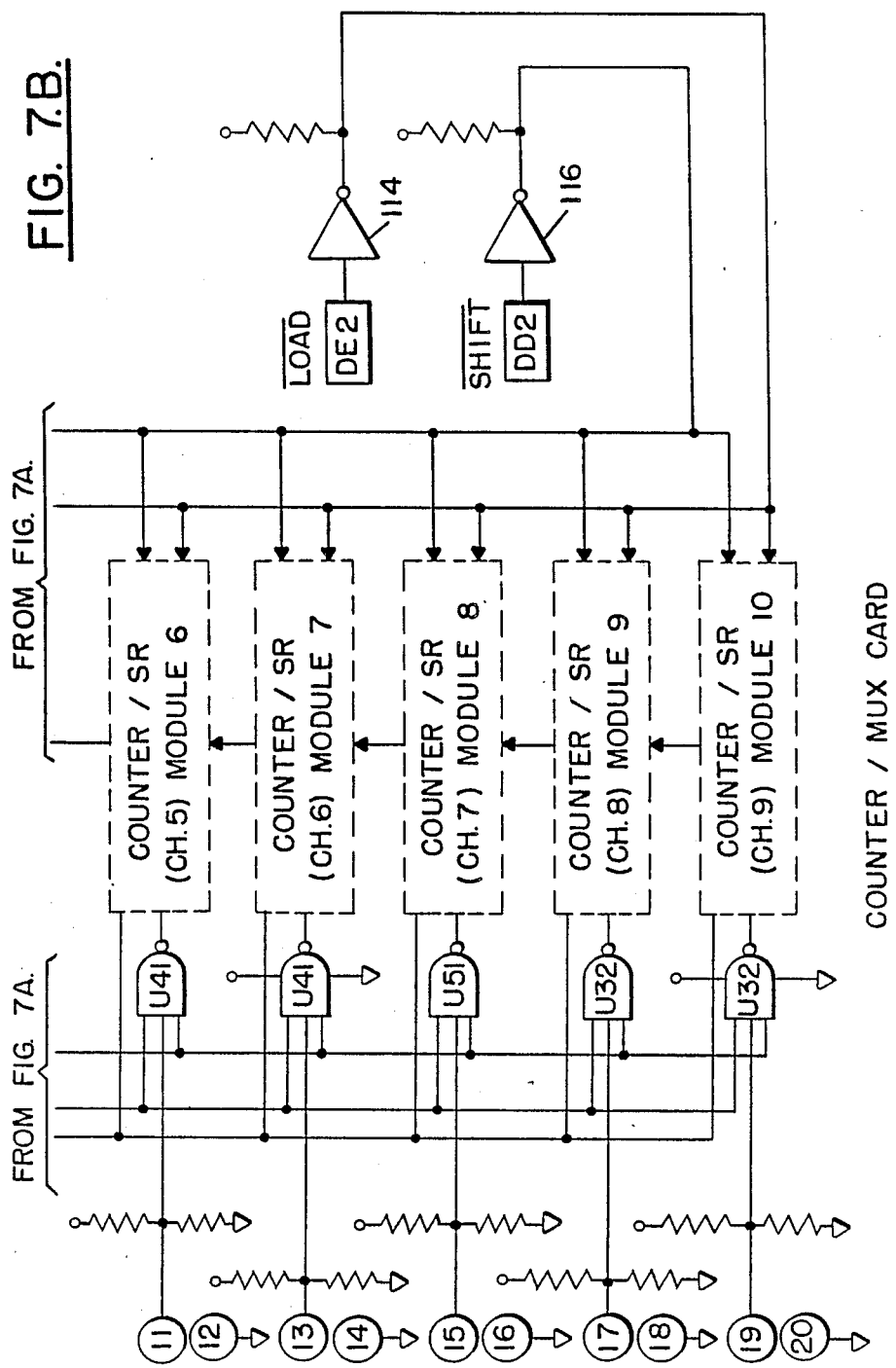

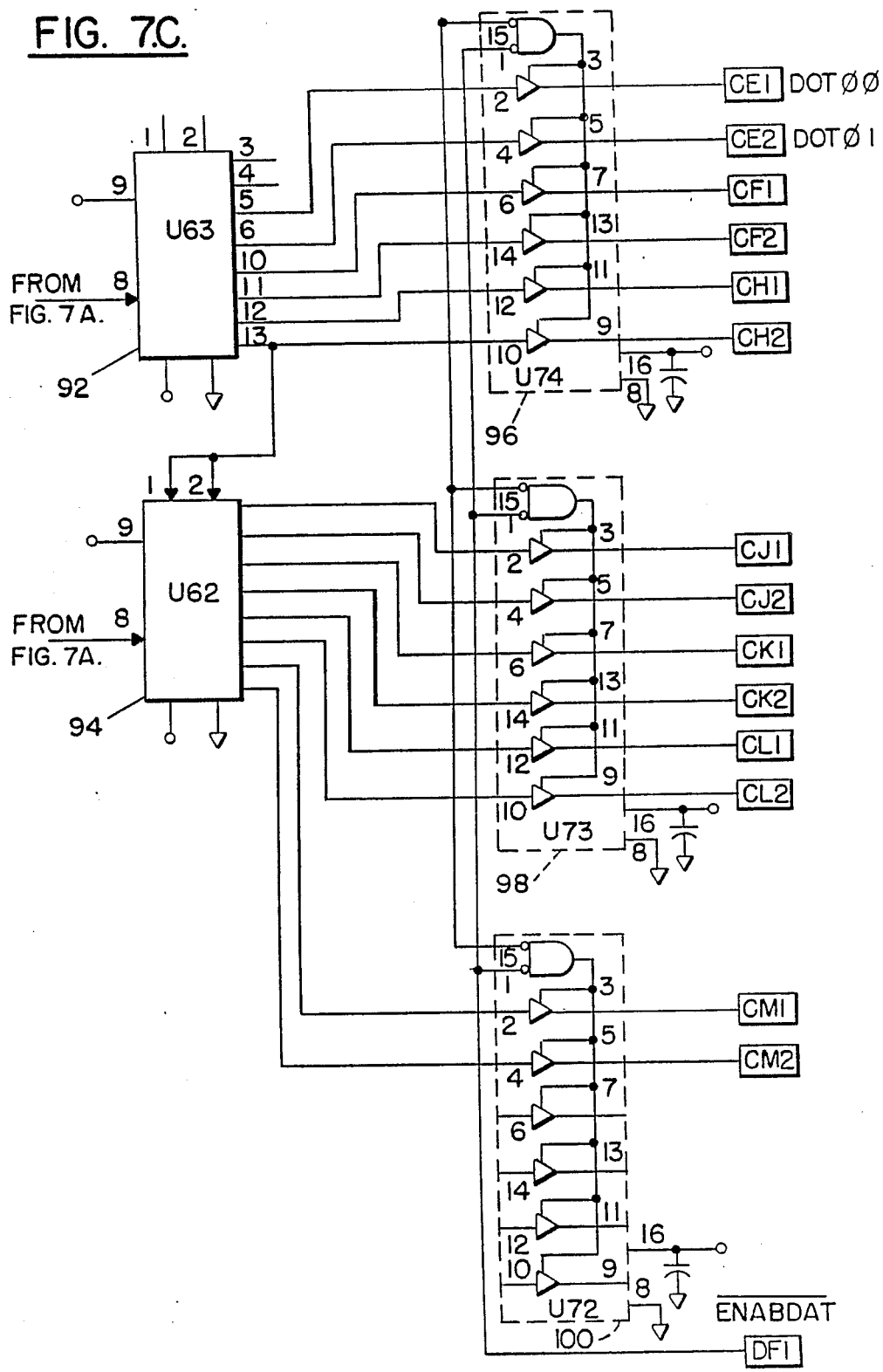

pBR 322 DNA 50 ng (LANE 1) AND 50 pg (LANE 2) IN 10 ug HUMAN DNA DIGESTED 1-1/2 HR. WITH Bgl I ENDONUCLEASE
AUTORADIOGRAPH : 36 HRS. AGA : 2 HRS. 18 mins.

METHODS AND APPARATUS FOR DETERMINING DISTRIBUTIONS OF RADIOACTIVE MATERIALS

This is a continuation of co-pending of application Ser. No. 170,042, filed on 3/11/88, now abandoned, which is a continuation of application Ser. No. 797,725, filed 13 Nov. 1985.

BACKGROUND OF THE INVENTION

1. Field of the Invention

This invention relates to methods and apparatus for determining distributions of radioactive materials. More particularly, it relates to methods and apparatus for determining distributions of radioactive materials wherein the distribution has been produced by a chromatography process, such as, an electrochromatography (electrophoresis) process.

2. Description of the Prior Art

By way of background, a variety of radioisotopes are currently used in chemical and medical research. Chromatographic procedures are routinely applied to separate isolate, and identify radioactively-labelled organic substances. The ability to effect such separation and identification of such radioactively-labelled materials has helped to increase their applications, especially in biochemical research. Thin-layer chromatography, column chromatographic techniques, electrophoresis, and paper chromatography can be used in suitable situations and have various sensitivities. Long-lived radioisotopes, which are generally weak beta emitters, are preferentially used for chemical and biological studies. Of particular importance are radiocarbon, $C^{14}$, and radioactive hydrogen (Tritium), $H^3$ Radioactive phosphorus, $P^{32}$, radioactive sulphur, $S^{35}$, and radioactive iodine, $I^{131}$, are also frequently used. Autoradiograms are limited in that no direct quantitative measurement of the relative strength of different bands is provided and that the procedures are often difficult to perform and require extended periods of time.

There are two major methods of detecting radiation in electro or other chromatograms: (i) autoradiography; and (ii) counting tubes and scintillation counters. Autoradiograms are produced as a result of the ability of alpha, beta, and gamma rays to darken photographic emulsions. The dry chromatogram is pressed against an X-ray film, wrapped, and kept in the dark for a period of time depending upon the nature of the radio isotopes involved. For example, $C^{14}$ labelled compounds are usually left in contact with X-ray film for 1-8 days; tritiated substances have to be exposed for more than a week; and $P^{32}$ or $I^{131}$ compounds can produce good autoradiograms in some cases in less than six hours. In the case of the detection of compounds containing different radioisotopes and double labelled substances on the same chromatogram, it is necessary to produce several autoradiograms over several months (i.e., the earlier autoradiographs would show spots caused by both isotopes, whereas the later autoradiographs would only show the isotope with the longer half life). Double emulsion radioautography, or mixed radioautography radiofluography can be used to detect dual labelled substances.

Paper chromatograms of radioactive substances can be quantitatively evaluated by a Geiger-Mueller counting tube, by use of a proportional counter, or by scintillation counting. Commercial devices for the detection and recording of material on an automatically transported paper strip or on a two-dimensional chromatogram are commercially available. Similar instruments for use with plates or gels are known.

Various patents have issued concerned with methods and devices for the detection of radioactively-labelled materials which have been chromatographically separated. Examples of such patents are: U.S. Pat. Nos. 3,027,453; 3,033,986; 4,019,057; 4,110,615; 4,311,908; 4,431,921; 4,028,549; 4,298,796; 3,814,939; 4,214,161; 4,267,451; 4,275,300; and 4,469,601. These publications are incorporated herein by way of reference.

In the field of biochemistry with particular reference to gene analysis, the standard technique for analyzing mixtures of polynucleotides involves the use of electrochromatography in combination with radioactive polynucleotide probes having known sequences. See E. Southern, "Gel Electrophoresis of Restriction Fragments," Methods in Enzymology, Vol. 68, 1979, pages 152-176.

In accordance with this technique, the mixture of polynucleotides to be analyzed is applied to a suitable electrophoresis gel, such as, an agarose or polyacrylamide gel, and an electric field is applied across the gel to separate the mixture into discrete bands. As a result of the separation, the polynucleotides in any particular band will in general have the same molecular weight and electrical charge.

Once the separation has been completed, denaturation is generally effected and a radioactive probe is applied to the gel and allowed to hybridize with the bands. The gel is then washed to remove unhybridized probe. As a result of this procedure, those bands, and presumably only those bands, which include polynucleotide sequences complementary to the probe sequence end up being radioactive. Radioactive bands can be obtained in other ways. For example, the mixture of polynucleotides to be analyzed can be radiolabeled, separated using electrophoresis, and then hybridized with cold probe. Non-hybridized sequences can then be removed using an enzyme, such as, mung bean nuclease or nuclease $S_1$, which preferentially breaks down single stranded polynucleotides. Again, the final product is a gel having discrete bands of radioactivity.)

Once the hybridization has been completed, the gels must be analyzed to determine where the radioactive bands are located. It is to this aspect of the overall process that the present invention is directed.

Prior to the present invention, the location of the radioactive bands has in most cases been determined through the use of X-ray films (autoradiography). Specifically, in the standard "Southern Blot" procedure, see E. Southern, *Methods in Enzymology, supra*, the radioactive bands in the gel have been transferred to a second medium, such as a sheet of cellulose nitrate paper, and a sheet of photographic film has been placed next to the second medium so that the radiation emitted by the radioactive bands ban locally expose the film. The film has then been developed using conventional techniques, and the bands analyzed visually to determine the presence or absence of specific polynucleotide sequences in the mixture of polynucleotides.

This photographic procedure has numerous disadvantages which are well known in the art. For example, it can often take exceedingly long periods of time to expose the film, e.g., periods of time on the order of week or more. Moreover, the process involves numerous manipulative steps both in terms of exposing the film and in terms of developing it. Overriding these physical problems is the fact that the ultimate output of the photographic process is simply a piece of film having a series of exposed bands therein. Output of this type has in general only been interpretable by skilled personnel.

In addition to the use of autoradiography, electrophorsis gels having radioactive bands have also been analyzed by scintillation counting. In this procedure the gel containing radioactive bands sliced or cut, dissolved in a certain scintillant, and subsequent light emissions are then measured. This procedure can produce quantitative results, but resolution is limited by the size of the slices of gel (typically 1 mm or greater).

Although one of the major applications of the invention herein described involves the analysis of genetic material, chromatography employing radioactive materials is also widely used in diverse chemical, and particularly biochemical, disciplines. As with gene analysis, in these fields radioactive materials become distributed in a supporting medium and there is a need to determine the distribution of those materials within the medium. Accordingly, the present invention is applicable to these fields also.

SUMMARY OF THE INVENTION

In view of the foregoing state of the art, it is an object of this invention to provide improved methods and apparatus for determining the distribution of a radioactive material in a medium. In particular, it is an object of the invention to provide automated methods and apparatus for making such determinations. In addition, it is an object of the invention to provide such methods and apparatus wherein the output produced is in an electrical form, suitable for computer processing.

To achieve the foregoing and other objects, the invention in accordance with certain of its aspects provides a method for determining the distribution of a radioactive material in a medium comprising the steps of:

(a) providing a plurality of radiation detectors at a set of predetermined locations, each of said detectors producing an electrical output indicative of the amount of radioactive material in the vicinity of the detector;

(b) moving the medium containing the radioactive material and the plurality of radiation detectors relative to one another so as to position the medium relative to the detectors at each of a set of predetermined positions; and (c) recording the electrical output of each of the detectors at each of the predetermined positions.

In accordance with others of its aspects, the invention provides an apparatus for determining the distribution of a radioactive material in a medium comprising:

(a) first means for locating a plurality of radiation detectors at a set of predetermined locations, each of said detectors producing an electrical output indicative of the amount of radioactive material in the vicinity of the detector;

(b) second means for receiving the medium containing the radioactive material;

(c) third means for moving the first and second means relative to one another so as to position the medium relative to the detectors at each of a set of predetermined positions and said movement means is amenable to computer control; and (d) fourth means for recording the electrical output of each of the detectors at each of the predetermined positions.

In accordance with certain preferred embodiments of the invention, the plurality of radiation detectors are arranged in a straight line and the medium and the detectors are moved relative to one another along a path parallel to that line. In accordance with these embodiments, it is further preferred for the predetermined locations of the detectors to be equally spaced from one another, for the predetermined relative positions of the medium and the detectors to be also equally spaced, and for the spacing between the predetermined positions to be smaller than the spacing between the predetermined locations.

In accordance with other preferred embodiments, Geiger-Mueller radiation detector tubes are used as the radiation detectors and the radiation emitted by the radioactive material in the medium is collimated before it reaches the Geiger-Mueller tubes.

The accompanying drawings, which are incorporated in and constitute part of the specification, illustrate the preferred embodiments of the invention, and together with the description, serve to explain the principles of the invention.

BRIEF DESCRIPTION OF THE DRAWINGS

FIGS. 7A, 7B and 7C are more detailed diagram of the circuitry shown in block form in FIG. 6.

DESCRIPTION OF THE PREFERRED EMBODIMENTS

As described above, the present invention relates to methods and apparatus for determining the distribution of radioactive materials in a medium. In the description which follows, the invention is discussed and illustrated with regard to its use in the field of gene analysis, and, in particular, with regard to its use in determining the distribution of a radioactive probe in an electrophoresis gel. It is to be understood that this description of the invention in this particular context is for purposes of illustration only and is not to be interpreted as limiting the applicability of the invention to other fields in which distributions of radioactive materials are to be determined.

With regard to the field of gene analysis, the present invention has particularly advantageous applications in the context of an automated gene analysis system of the type described in copending U.S. patent application Ser. No. 497,997, filed May 25, 1985, and entitled "Apparatus and Method for Separating Polynucleotides and Detecting Specific Polynucleotide Sequences," the pertinent portions of which are incorporated herein by reference. See also European Patent Publication No. 134,622, published Mar. 20, 1985, which corresponds to the above U.S. patent application.

Figure 1:
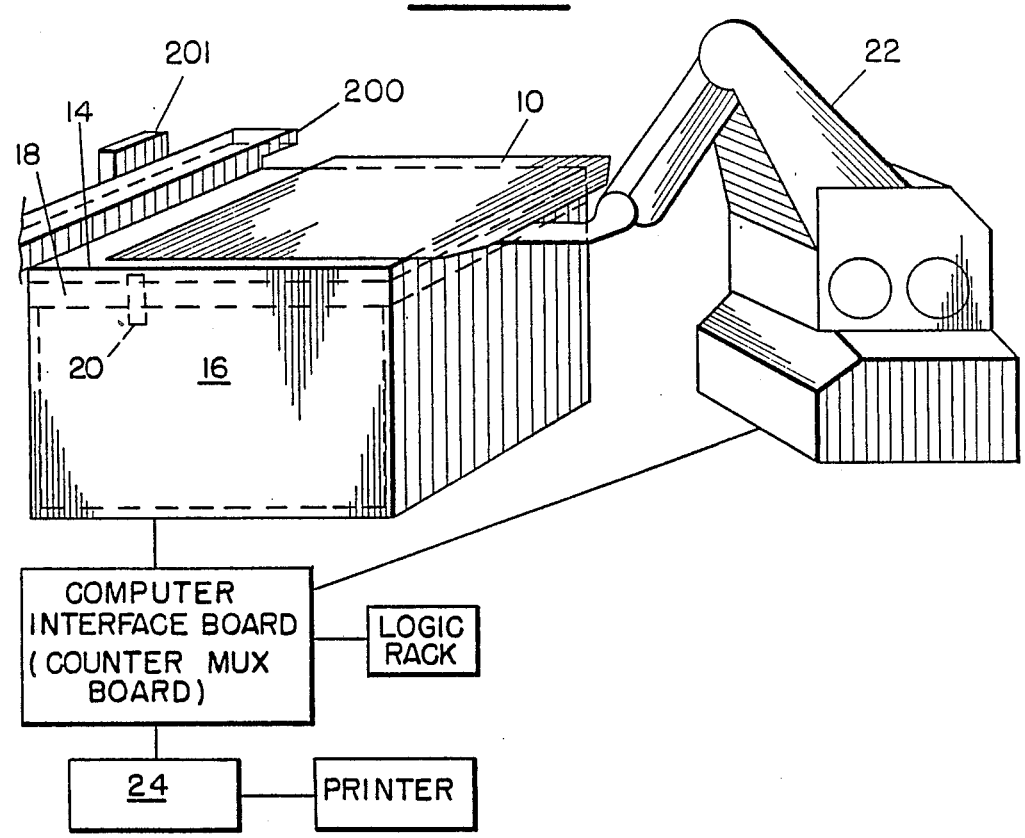
FIG. 1 shows an overall arrangement of apparatus suitable for practicing the present invention.

Referring now to the figures, there is shown in FIG. 1 an overall schematic view and block diagram of apparatus suitable for practicing the present invention. Four main components are shown: (1) frame 10 for receiving electrophoresis gel 12; (2) frame 14 to which are attached electronic module 16 (printed circuit board; 1 board/lane servicing 10 Geiger-Mueller tubes) and radiation detector mounting blocks 18, which carry Geiger-Mueller radiation counter tubes 20; (3) robot 22, [e.g., a modified Armdroid 1 (Colne Robotics Co., Ltd., Twickenham, England], for moving frame 10 and thus electrophoresis gel 12 past counter tubes 20; and (4) computer 24, [e.g., a general purpose microcomputer, such as Radio Shack TRS 80 Model 4, or equivalent can be used], for controlling the operation of robot 22 and electronic module 16 and for receiving and processing electrical output from module 16.

The modifications of the Armdroid 1 robot specified above are described in copending patent application Ser. No. 797, 729 (this application is a continuation-in-part of Ser. No. 497,997, filed May 25, 1983 and entitled "Apparatus and Method for Separating Polynucleotides and Detecting Specific Polynucleotide Sequences").

Referring to FIG. 1, tray 200 can optionally be attached to the detector and can be used for storage of weight 201. The weight 201 can be placed on top of the gel frame of the invention for stabilization purposes during the detection process.

Figure 2:
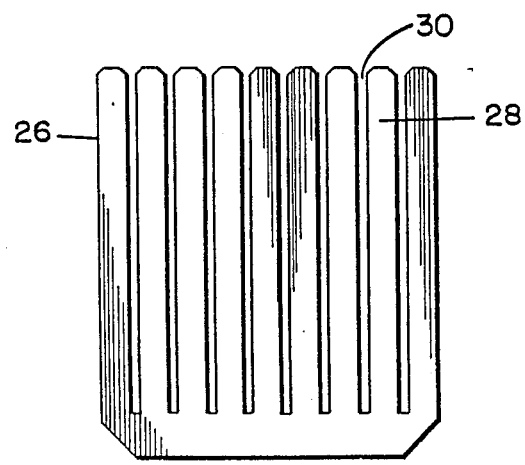
FIG. 2 shows an electrophoresis gel containing radioactive bands, the locations of which can be determined using the apparatus of FIG. 1.
Figure 2A:
FIG. 2A shows a side view of the electrophoresis gel of FIG. 2.
Figure 3:
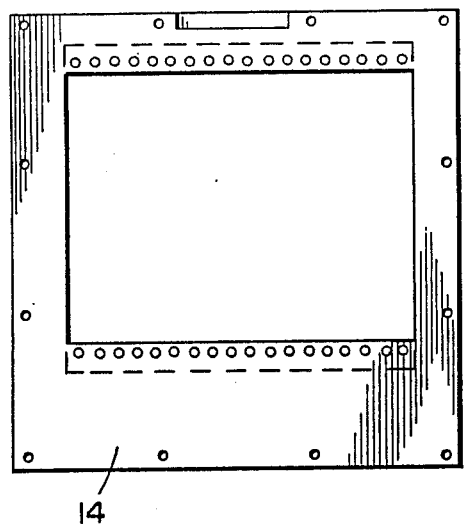
FIG. 3 shows a frame for receiving the electrophoresis gel of FIG. 2.

Electrophoresis gel 12 and frame 10 are shown in more detail in FIGS. 2 and 3, respectively. As shown in FIG. 2, gel 12 is supported on backing 26 and includes nine individual tracks 28 separated from one another by open spaces 30. Although the invention will be illustrated with regard to the multi-track gel shown in FIG. 2, it is to be understood that the invention is equally applicable to a single track gel. Each of tracks 28 includes radioactive bands created by a hybridization process of the type described above. For typical radiolabeled nucleotides, the bands will emit beta particles, it being understood, of course, that the present invention is equally applicable to other types of emitted radiation, e.g., gamma rays.

Gel 12 is preferably an agarose gel having a thickness of less than about 1.5 mm. See U.S. patent application Ser. No. 497,997, referred to above. Backing 26 can be made of a polycarbonate plastic and can have a thickness of about 0.062 inches. Support membrane 36 attenuates the radiation emitted.

Figure 3A:
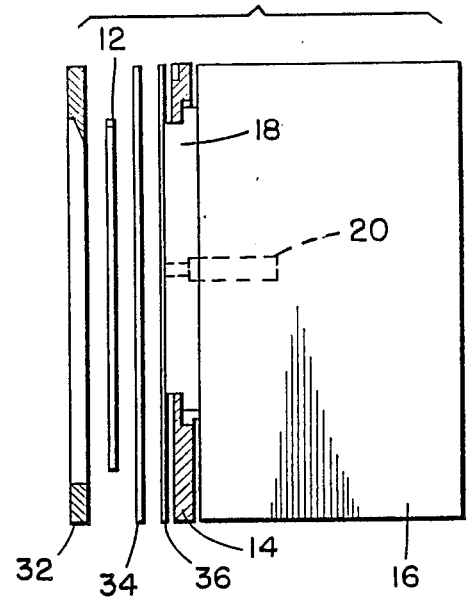
FIG. 3A is a side view of frame 14.
Figure 3B:
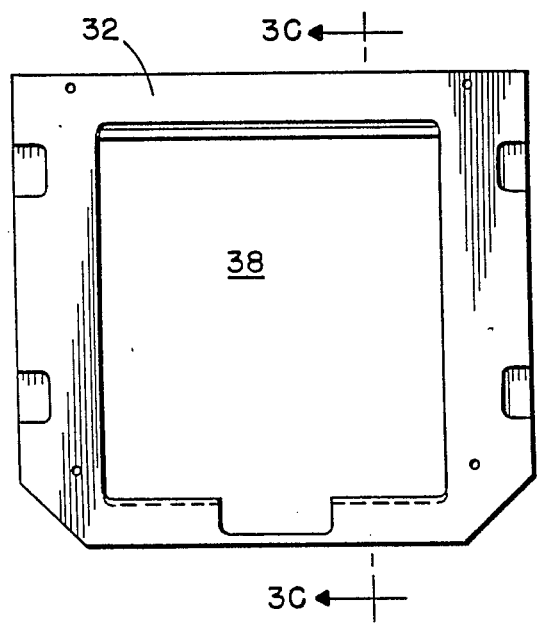
FIG. 3B is a top view of frame portion 32.
Figure 3C:
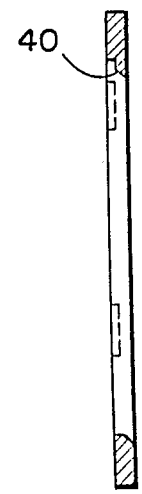
FIG. 3C is a side view of frame portion 32.
Figure 3D:
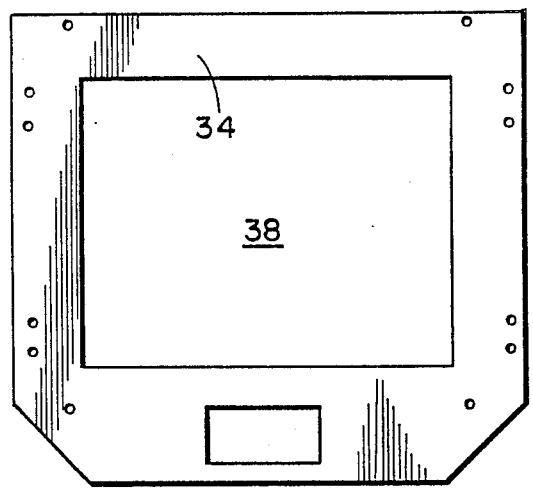
FIG. 3D is a lower view of frame portion 34.
Figure 3E:
FIG. 3E is a side view of frame portion 34.

As shown in FIGS. 3-3E, frame 10 is composed of three parts: upper portion 32, lower portion 34, and support membrane 36. The upper and lower portions of the frame are attached to each other by, for example, screws, and together form opening 38 for receiving gel 12. Support membrane 36 forms the bottom of opening 38 and is attached to lower portion 34 by, for example, being glued thereto. Support membrane 36 can be composed of mylar or vinyl and can have a thickness of about 0.003 inches, for the purpose of minimizing radiation attenuation. Upper portion 32 includes chamber 40 which aids robot 22 in placing gel 12 in opening 38.

FIG. 3 shows a top view of frame 14; FIG. 3A shows a side view of frame 14; electronic circuit board 16; Geiger-Mueller tube 20; mounting block 18; membrane 36; lower portion of frame 10, (34); gel 12; and upper portion of frame 10 (32). FIG. 3B shows a top view of upper portion 32; opening 38. FIG. 3C is a side view of 32 showing chamber 40. FIG. 3D is a top view of lower portion 34; opening 38. FIG. 3E is a side view of 34.

Figure 4:
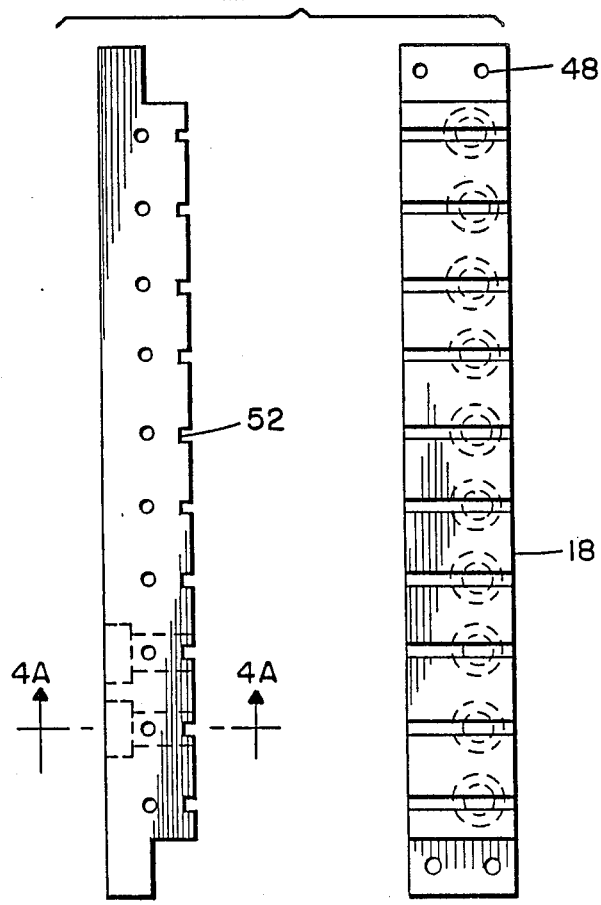
FIG. 4 shows a mounting block for locating a plurality of Geiger-Mueller tubes at predetermined locations.
Figure 4A:
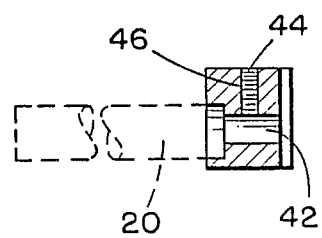
FIG. 4A is a cross-sectional view along lines 4A-4A in FIG. 4.

Turning now to FIG. 4, this figure shows in greater detail one of the radiation detector mounting blocks 18 carried by frame 14. In total, nine detector blocks are attached to frame 14, one for each of electrophoresis gel tracks 28.

Block 18, which can be made of a metal, such as, brass, includes a plurality of bores 42 for receiving Geiger-Mueller tubes 20. Although shown offset from the center line of block 18, when assembled onto frame 14, tubes 20 lie along the center lines of gel tracks 28. Conventional Geiger-Mueller tubes, including an anode and cathode sealed within a stainless steel housing filled with a counting gas mixture are used. A suitable Geiger-Mueller tube for use with the present invention is LND Co. Model 715.

As shown in FIG. 4, a total of ten Geiger-Mueller tubes are carried by block 18, the tubes being equally spaced from one another. For analyzing electrophoresis gels, a spacing between tubes on the order of approximately 12 mm (center-to-center) has been found suitable, although larger and smaller spacings can also used.

Geiger-Mueller tubes 20 are held in bores 42 by means of set screws 44 which pass through threaded bores 46 and engage the outer housing of tubes 20. Block 18 also includes bores 48 for attaching block 18 to frame 14, as well as bores 50 for attaching portions of electronics module 16 to block 18.

To collimate the radiation being emitted from gel 12 before the radiation reaches tubes 20, block 18 includes throughs 52 which extend across the top surface of the block. For the Geiger-Mueller tubes described above, it has been found suitable to use throughs having a width of approximately 1 mm and a depth of approximately 0.015 inches. The throughs intersect bores 42 to produce a rectangular window having a width of approximately 1 mm and a length of approximately 0.180 inches through which radiation can reach detector tubes 20. By collimating the radiation in this way, it has been found that each Geiger-Mueller tube is primarily responsive to the transverse portion of the gel nearest the tube and not particularly responsive to transverse portions ahead or behind the nearest portion.

Figure 5:
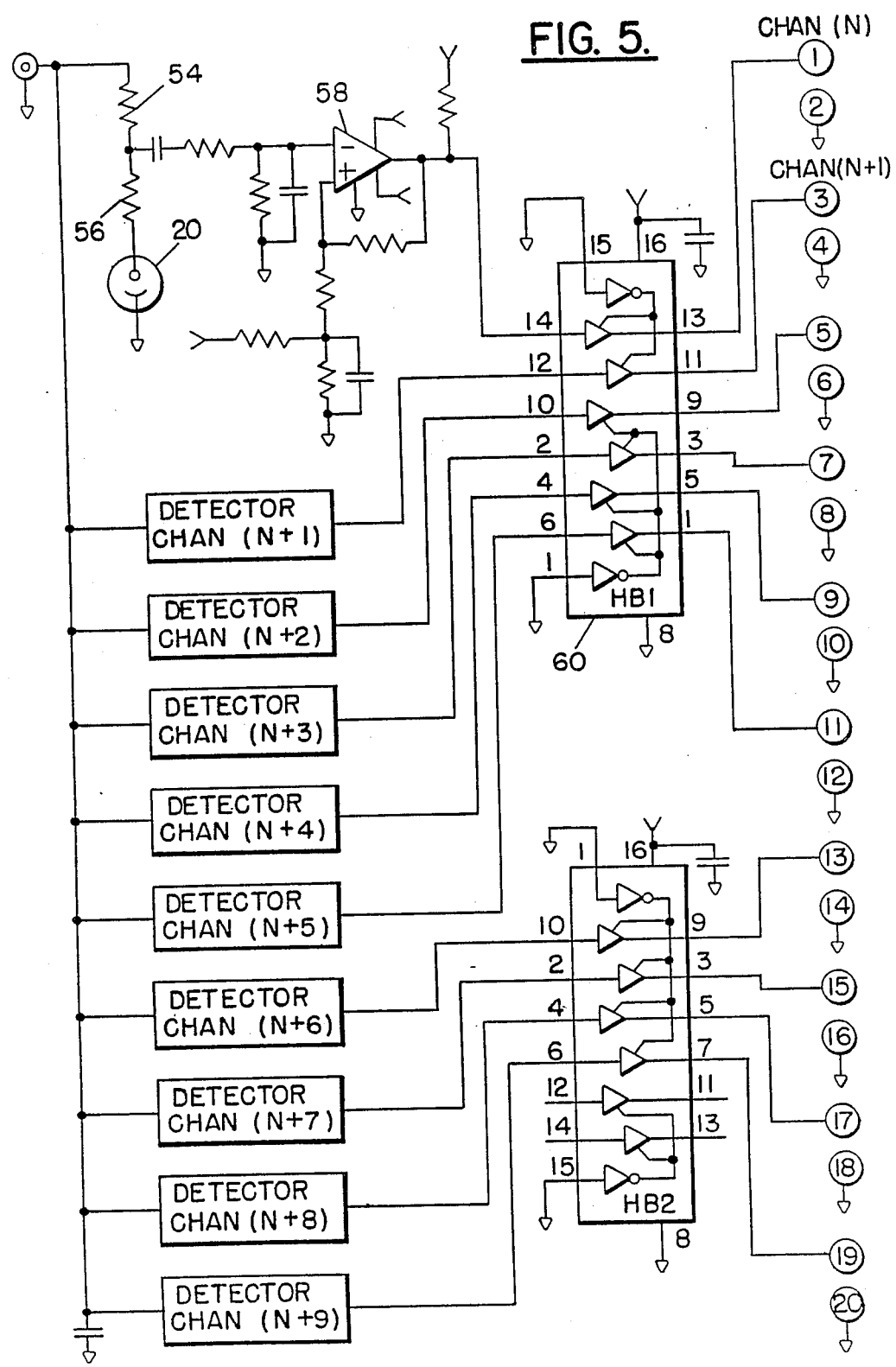
FIG. 5 is a circuit diagram showing suitable circuitry for powering the Geiger-Mueller tubes of FIG. 4, as well as for converting the output of those tubes into digital pulses.

Referring now to FIG. 5, there is shown in this figure circuitry suitable for powering the ten Geiger-Mueller tubes carried by one of blocks 18. The circuitry also converts the output of the Geiger-Mueller tubes into digital pulses which can be recorded by the circuit of FIG. 6 and 7, and subsequently processed in computer 24. The circuitry of FIG. 5 can conveniently be mounted on a single circuit board which can be attached directly to block 18 by means of bores 50. As will be evident, the circuitry of FIGS. 5, 6, and 7 is repeated for each of blocks 18.

As shown in FIG. 5, each Geiger-Mueller tube 20 is provided with a high voltage, e.g., +500 volts, through resistors 54 and 56. When radiation of a sufficiently high energy passes through the Geiger-Mueller tube, the gas breaks down producing a spike at the negative input of LM311N comparator 58. If the magnitude of the spike exceeds the threshold value set at the comparator's positive input, e.g., 1.7 volts, the comparator outputs a pulse having a nominal value of +3 volts. This pulse is fed into SN74367 buffer 60 and then to the recording circuitry of FIGS. 6 and 7.

It has been found that the presence of sharp edges at the connection of resistor 56 to detector tube 20 can result in false pulses being produced by the circuitry of adjacent detectors when one detector fires. To avoid this problem, it has been found advantageous to use Geiger-Mueller tubes of the type described above and to directly connect resistor 56 to those tubes using the screw-on cap which forms the top part of the tubes.

Figure 6:
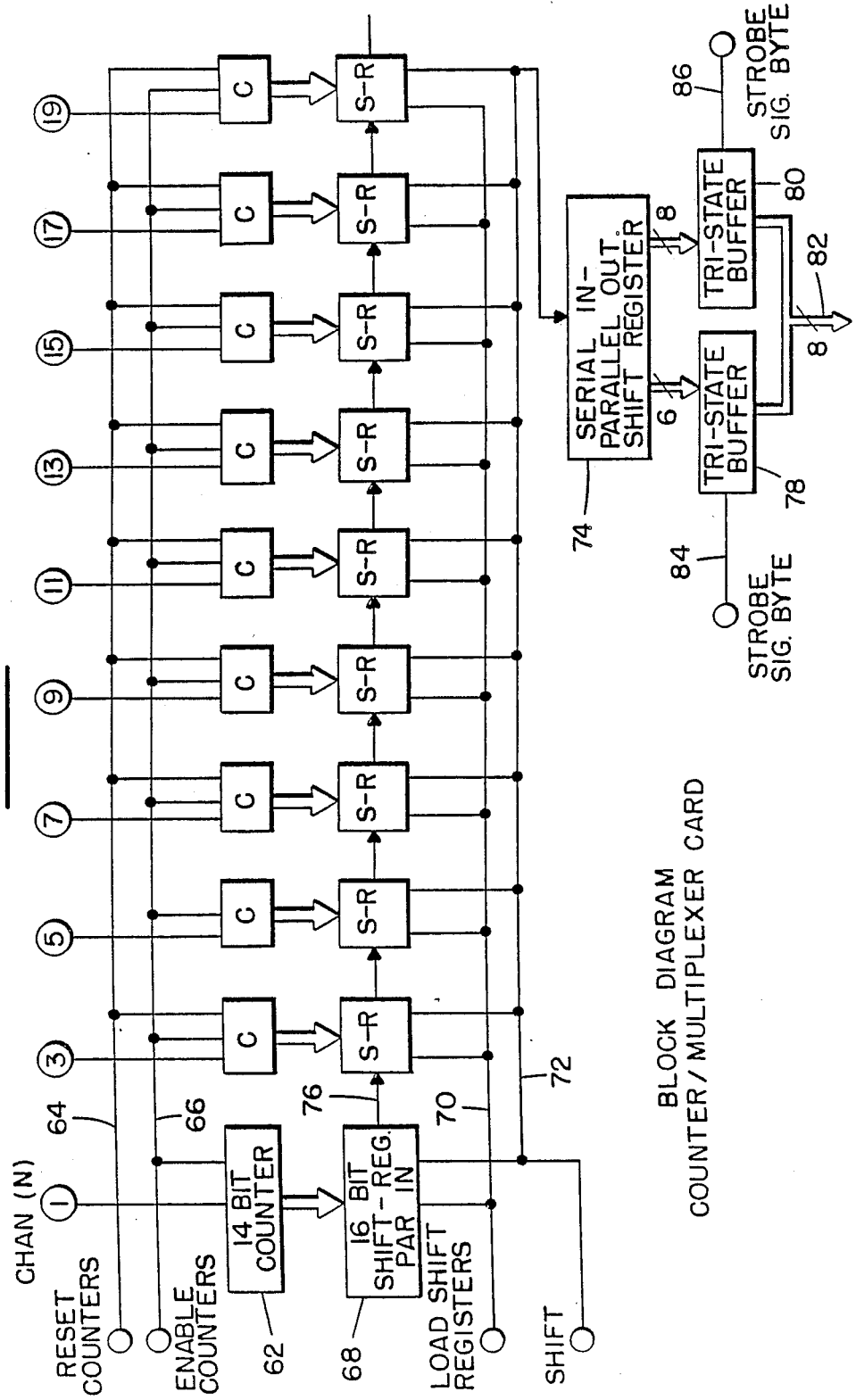
FIG. 6 is a block diagram of circuitry suitable for recording the digital pulses generated by the circuit of FIG. 5 and for transferring the recorded values to a digital computer for further processing.
Figure 7A:
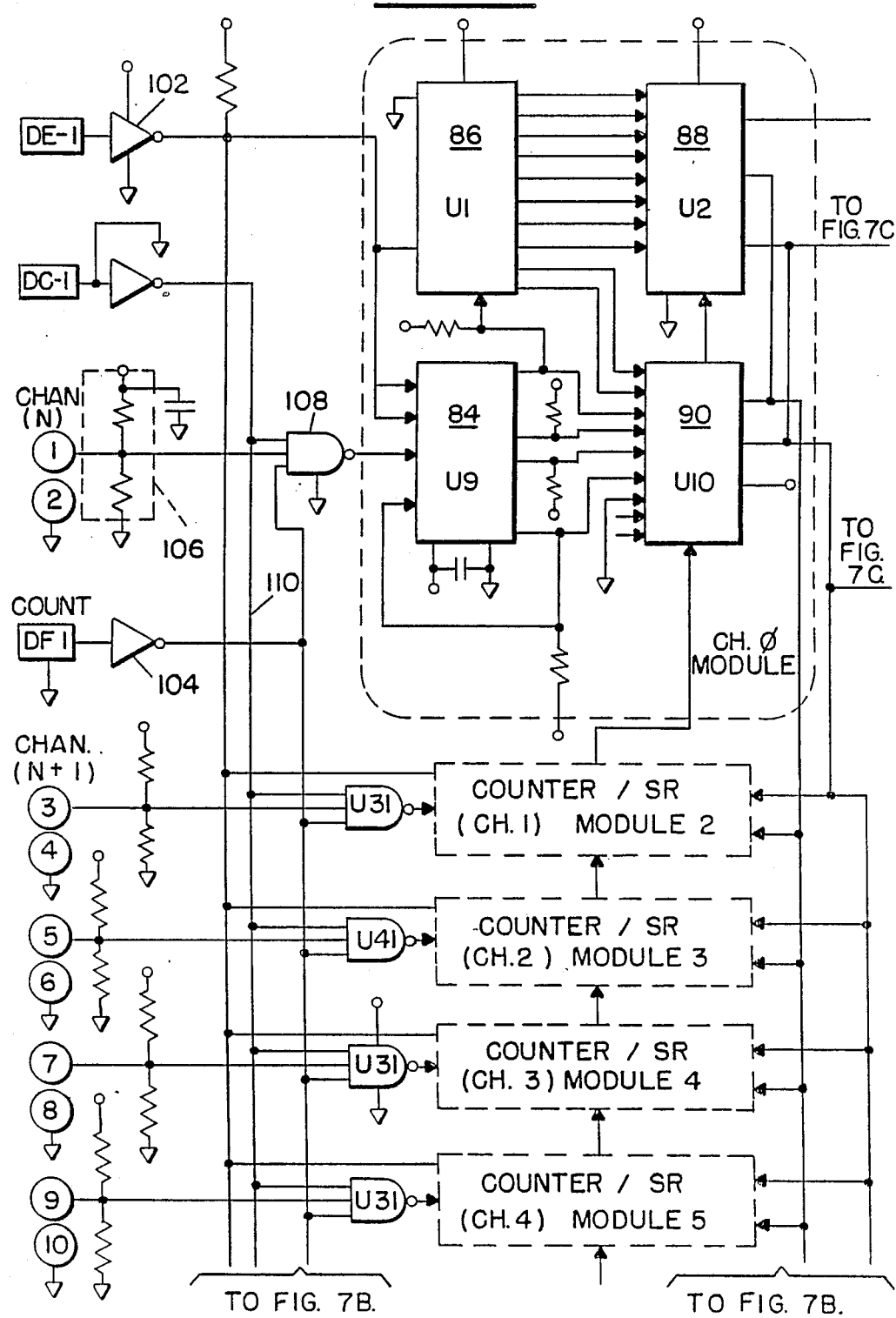

The recording circuitry of FIGS. 6 and 7 receives the output of the circuitry of FIG. 5 at the terminals identified by the numbers 1 through 20 and produces output suitable for subsequent inputting to a microcomputer at the terminals identified by the designations CE1, CE2, CF1, CF2, CH1, CH2, CJ1, CJ2, CK1, CK2, CL1, CL2, CM1, and CM2 (D0T00 through D0T13). The circuitry is also designed to receive inputs originating from the microcomputer at terminals DD2, DE1, DE2, DF1, DF2, and DU2. As explained below, these inputs control the flow of data from the detectors to the recording circuitry and from the recording circuitry to the computer. Depending upon the microcomputer used, its programming, and the physical layout of the components, it may be convenient to use interface/-buffer circuits of the type illustrated in FIG. 8 between the microcomputer and the circuitry of FIGS. 6 and 7.

The overall operation of the recording circuitry can best be seen by reference to FIG. 6. The output from buffers 60 is recorded by 14-bit counters 62. Connected to the counters are counter reset line 64 and counter enable line 66. At the beginning of each counting period, computer 24 causes a reset signal to be sent along line 64 which resets the total of each of counters 62 to zero. Thereafter, the computer causes an enable signal to be sent along line 64 which turns on the counters for a predetermined amount of time, e.g., 30 seconds, during which time the counters record the number of electrical pulses generated by the Geiger-Mueller tubes.

Connected to counters 62 are shift registers 68. These registers are of the parallel in/serial out type. Connected to the registers are load line 70 and shift line 72. At the end of each counting period, computer 24 causes a load signal to be sent along line 70 which causes the number of counts recorded by the counters to be loaded into the shift registers. Thereafter, the computer causes 16 shift signals to be sent to the shift registers along shift line 72. 16 shifts are necessary because two 8-bit shift registers (SR) are used. These shift signals cause the contents of the tenth shift register to be loaded into serial in/parallel out shift register 74, and the contents of all the remaining shift registers to be loaded into the next downstream register by means of lines 76.

The information in shift register 74 is sent to computer 24 by means of data bus 82 and tri-state buffers 78 and 80. Specifically, computer 24 causes a strobe signal to be inputted into buffer 78 along line 84, allowing that buffer to transfer its contents to bus 82 and thus to the computer. Thereafter, a strobe signal is inputted into buffer 80 along line 86, allowing that buffer to transfer its contents to the computer.

Once the contents of the tenth shift register have been transferred to computer 24, sixteen additional shift signals are sent to the shift registers along shift line 72, causing the contents of the ninth shift register to move into serial in/parallel out shift register 74, and the contents of all the other shift registers to move one shift register downstream. The new contents of shift register 74 is then transferred to the computer following the same procedure as described above, and the process is repeated eight more times until the contents of all the shift registers have been loaded into the computer. It is important to note that while this loading of data into the computer is taking place, counters 62 can be enabled so that counting of pulses can take place simultaneously with data transfer to the computer.

Figure 8:
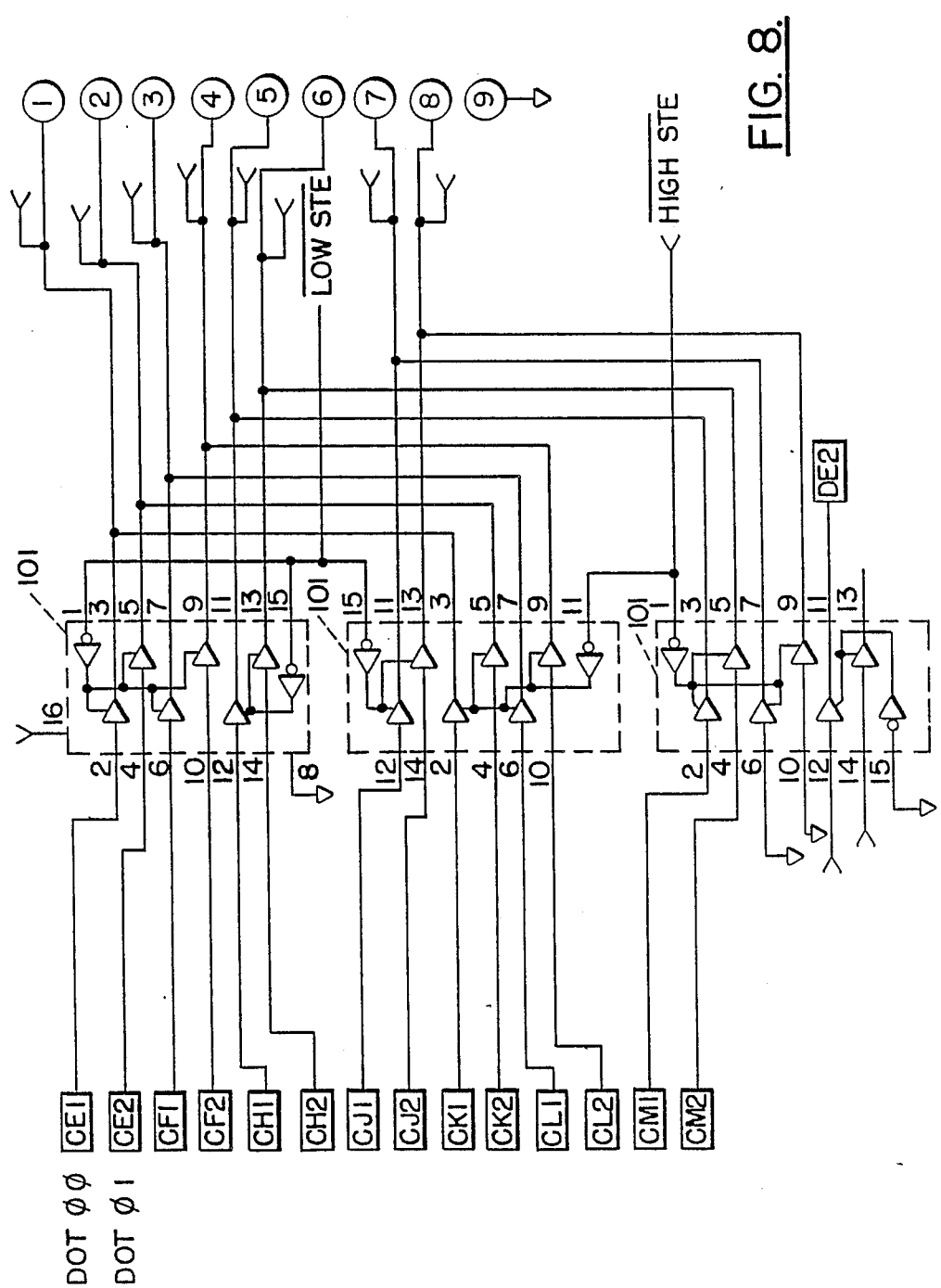
FIG. 8 is a diagram of an interface circuit for use with the circuit of FIG. 7 for transferring data into a digital computer.

Specific apparatus for implementing the circuit of FIG. 6 is shown in FIGS. 7 and 8. As shown therein, fourteen bit counters 62 can be composed of a SN74LS93 counter 84 connected to a MC14040BAL counter 86. Parallel in/serial out shift registers 68 can be composed of two MC14021BAL shift registers 88 and 90. Serial in/parallel out shift register 74 can be composed of two SN74LS164 shift registers 92 and 94. Tri-state buffers 78 and 80 can be composed of three SN74LS365 buffers 96, 98 and 100 (only part of buffer 100 is used) in combination with the interface circuit of FIG. 8 which employs three LS367 buffers 101.

Resetting of the counters occurs through terminal DE1 and SN7404 inverter 102. Counting is enabled through terminal DF2 and SN7404 inverter 104. Pulses from buffers 60 enter the counters through 314E221331 terminators 106 and SN74LS510 NAND gates 108. In addition to the pulse signal and the enable signal, NAND gates 108 also receive a high input along line 110 from SN7404 inverter 112. Loading of the counter totals into the parallel in/serial out shift registers occurs through terminal DE2 and SN7404 inverter 114. Downstream shifting from shift register to shift register occurs through terminal DD2 and SN7404 inverter 116. Strobing of the tri-state buffers occurs through terminal DU2, which selects the set of Geiger-Mueller tubes from which data is to be transferred to the computer, terminal DF1 which enables buffers 96, 98, and 100, and the NOT LOW STB and NOT HIGH STB inputs of FIG. 8 which determine whether the most or least significant bits at terminals CE1, CE2, CF1, CF2, CH1, CH2, CJ1, CJ2, CK1, CK2, CL1, CL2, CM1, and CM2 (D0T00 through D0T13) are transferred to terminals DB0IN through DB7IN.

With reference to FIG. 1, the operation of the apparatus is as follows. Robot 22, which is under the control of computer 24, places electrophoresis gel 12 into frame 10 and positions that frame with respect to stationary frame 14 at a first predetermined position wherein gel tracks 28, which include the radioactive bands whose positions are to be determined, lie over Geiger-Mueller tubes 20, with the left hand edge of the tracks (as seen in FIG. 1) being positioned over the tenth detector tube for each track.

Next, the computer resets and then enables 16-bit counters 62 for a predetermined period of time, e.g., 30 seconds, during which time the counters record the number of pulses generated by the detector tubes. Thereafter, the computer causes the contents of counters 62 to be loaded into 16-bit shift registers 68.

Upon the completion of loading, robot 22 moves frame 10 and gel 12 to the left (as seen in FIG. 1) so as to place the gel and the detectors at a second predetermined position with respect to one another. For Geiger-Mueller tubes of the type described above and for a 12 mm spacing between tubes, it has been found convenient to move the gel with respect to the tubes in increments of either 1 mm, for higher speed scans, or $\frac{1}{2}$ or $\frac{1}{4}$ mm, for higher resolution scans. In this way, a complete gel can be scanned in 12, 24, or 48 steps for the 1, $\frac{1}{2}$, and $\frac{1}{4}$ mm increments, respectively. In terms of time, for a recording period of 30 seconds at each position, this corresponds to scan times of from 6 to 24 minutes for a complete gel. Other convenient recording periods may be conveniently employed.

Once the gel has been located at its new position, data recording is again commenced by resetting and then enabling counters 62. During both moving of the gel and, if need be, during the initial recording of data at the new location, data is transferred to computer 24 from shift registers 68. In this way, no time is lost waiting for data transfer to be completed from the 90 detectors (10 detectors per gel track ×9 gel tracks). The record-move-record process with simultaneous data transfer is repeated until the entire gel has been scanned.

Once all of the data has been transferred to computer 24, it can be displayed, processed and analyzed using standard data manipulation techniques. For example, the data can be smoothed by using a hanning window-type software filter.

Although specific embodiments of the invention have been described and illustrated, it is to be understood that modifications can be made without departing from the invention's spirit and scope. For example, rather than using a robot to move the gel past the detectors, a separate motor (stepper motor) can be employed for this purpose. Similarly, a variety of circuits and circuit components other than those shown can be used to practice the present invention.

During the operation of the detector of the invention, the weight 201 stored in tray 200 as shown in FIG. 1 may optionally be placed on top of gel 12 in order to maintain contact with the detector during the measurement of radioactivity.

The following non-limiting Examples further serve to illustrate the invention.

EXAMPLE 1

Detection of $P^{32}$ DNA Probe

Figure 9:
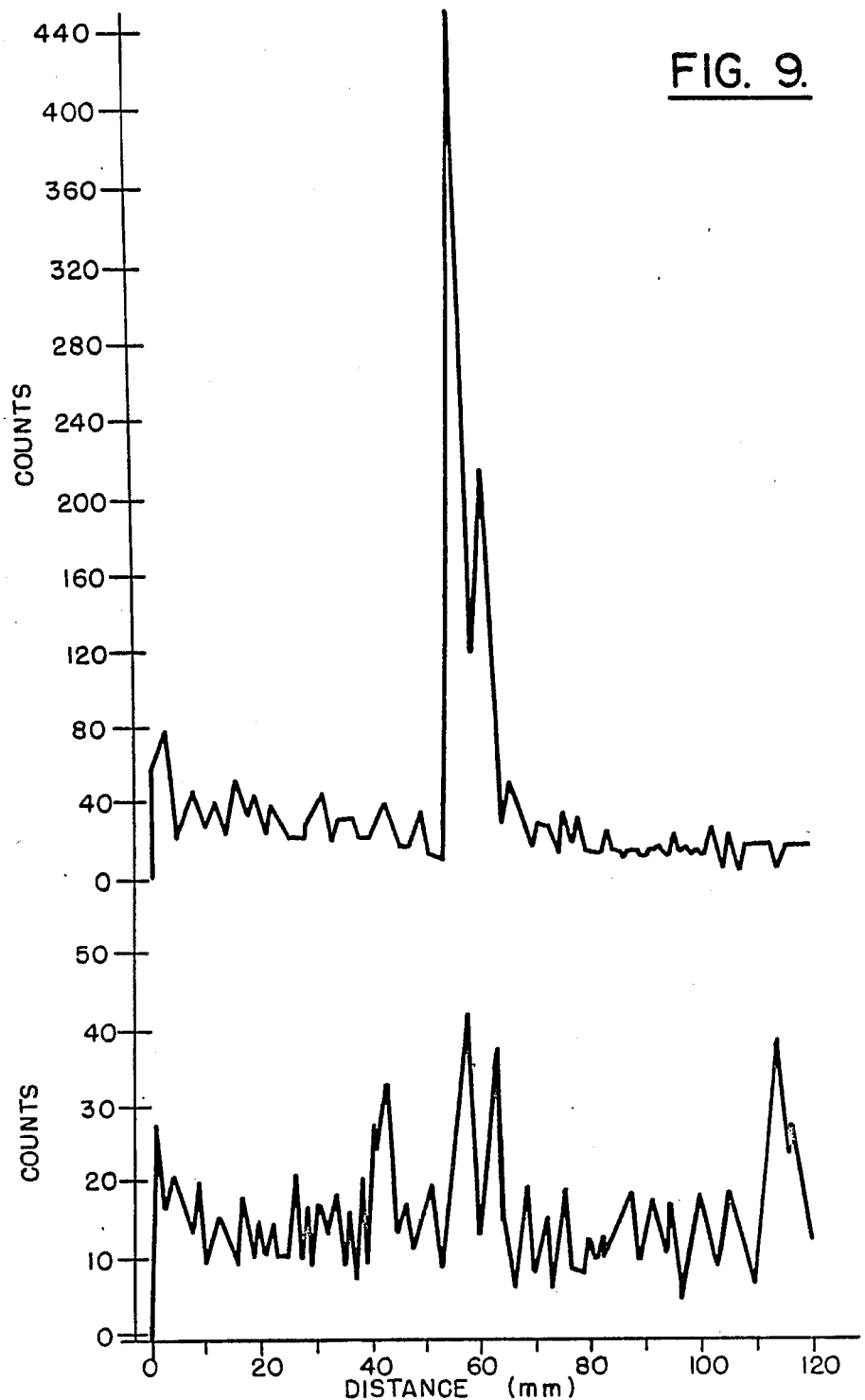
FIG. 9 is a graph comparison and autoradiogram showing comparison of the detection of bacterial DNA (pBR322 DNA) in the presence of human DNA.

An experiment was designed to compare detection of radioactively-labelled compounds on the electrophoresis gel using the apparatus previously described (continuation-in-part application Ser. No. 797,729, filed Nov. 13, 1985 and entitled "Apparatus and Method for Separating Polynucleotides and Detecting Specific Polynucleotide Sequences") and including detector of the invention with autoradiography detection of the same sample. A sample of human DNA from blood was extracted and purified using the technique described in Maniatis et al., Molecular Cloning, Cold Springs Harbor Laboratory, pp. 104–106 (1982), and digested 1½ hours with BglI endonuclease. pBR322 DNA was purchased from Bethesda Research Labs. and similarly cut with BglI. These bacterial and human samples of DNA were then separated by gel electrophoresis using a thin agarose gel. The gel was dried for 10 minutes in a microwave-vacuum dryer. The microwave dryer is described in copending U.S. patent application Ser. No. 343,256, filed Jan. 27, 1982. Denaturation of the separated material was effected using NaOH. The sample was then prehybridized to block all extraneous sites by circulation in a prehybridization mixture containing: 50% formamide (v/v); 5×Denhardt's Soln; 5×SSPE (per/1 43.5 g NaCl; 6.9 g $NaH_2PO_4.H_2O$; 1.85 $Na_2.EDTA$; pH 7.4); 400 mg/ml Salmon Sperm DNA; and 0.19 (v/v) SDS (Sodium Dodecyl Sulfate), and hybridized with a single-stranded $P^{32}$ pBR322 DNA probe. Following hybridization, the sample was washed twice with SSC (standard saline citrate per/1: 8.76 g $NaCl_2$: 4.41 g Na.Citrate, pH 7.0), then 0.1×SSC, then water, dried again using a microwave dryer, and evaluated. An autoradiograph of 36 hours duration was obtained, and the detector of the invention was used to obtain a graphic evaluation in 2 hours, 18 minutes (at a rate of 11.5 minutes of counting/mm traversed). Results of this experiment are presented in FIG. 9. It can be seen that the detector of the invention rapidly produces a graphic quantitative measurement of the different bands of the gel.

EXAMPLE 2

Detection of $P^{32}$ Lambda DNA

Figure 10:
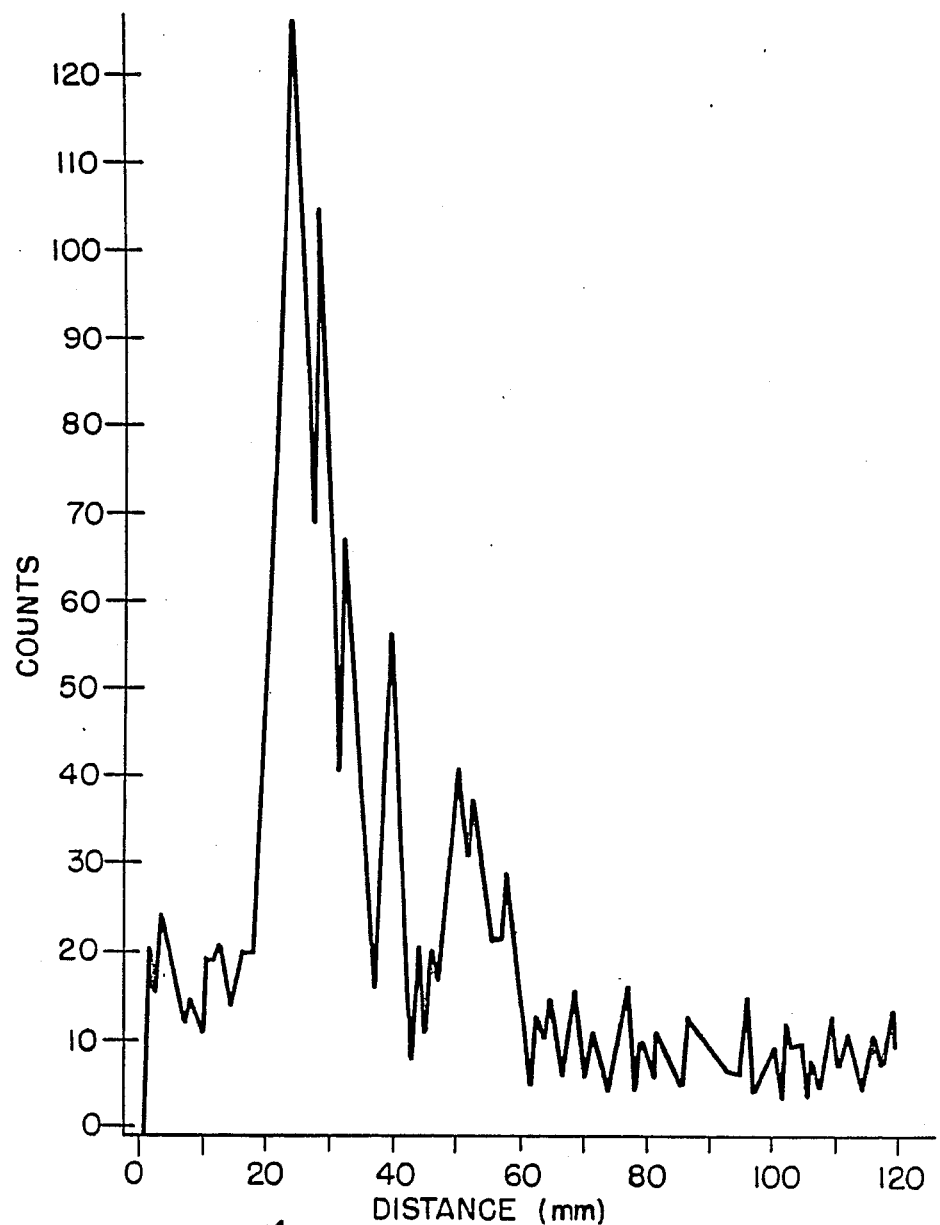
FIG. 10 is a graph and autoradiogram showing comparison of the detection of radio-labelled lambda DNA.

A similar experiment to Example 1 above was performed using a sample of lambda phage DNA digested with HindIII and the methods of Example 1. A $P^{32}$ probe of lambda DNA digest was used. The resultant gel was radiofluorographed 33 hours and evaluated by the detector of the invention at the rate of 10 minutes/mm for a total time of 2 hours. Results of this experiment are presented in FIG. 10. The detector of the invention rapidly produces a graphic quantitative measurement of the radiolabelled bands of the gel.

What is claimed is:

1. A method for determining the quantitative distribution of bands of a radioactive material spaced lengthwise along a medium which is in the form of a narrow elongated track, said radioactive material comprising a radioactive isotope which emits radiation, said method comprising the steps of:
   (a) providing a plurality of identical radiation detectors at a set of predetermined locations spaced along the length of the track, said radiation detectors being arranged in a straight line, said predetermined locations being equally spaced from one another, center-to-center, by a distance D, and each of said detectors producing an electrical output indicative of the amount of radioactive material in each said band in the vicinity of the detector;
   (b) moving the medium containing the radioactive material and the plurality of radiation detectors relative to one another in a step-like manner only along a path parallel to the straight line and parallel to the long axis of the track so as to position the medium and radioactive bands relative to the detectors at each of a plurality of predetermined positions which are equally spaced from one another by a distance d, the spacing D between the predetermined locations being several times greater than the spacing d between the predetermined positions, the total relative movement of the medium and the plurality of radiation detectors being equal to the spacing D between the predetermined locations;

(c) simultaneously measuring the amount of radioactive material in each of the bands in the vicinity of each of the detectors after each step at each of the predetermined positions by means of the electrical output produced by the individual detectors; and (d) recording the electrical output of each of the detectors at each of the predetermined positions to produce simultaneous measurements of the amount of radioactive material in each of the spaced bands along the elongated track.

2. The method of claim 1 wherein the spacing between the predetermined locations is greater than the spacing between the predetermined positions by a factor of 10 or more.

3. The method of claim 1 wherein the relative motion between the plurality of radiation detectors and the medium is achieved by holding the detectors stationary and moving the medium past the detectors.

4. The method of claim 1 including the additional step of providing identical collimating means between the medium and each of the detectors for collimating the radiation emitted by the radioactive material in the medium before said radiation reaches the detectors, each said collimating means forming a rectangular through in front of each of the detectors, the long axis of the rectangle extending across the width of the track so that each detector is primarily responsive to the transverse portion of the track nearest the detector rather than transverse portions of the track ahead or behind the nearest portion.

5. Apparatus for determining the distribution of a radioactive material in a medium which is in the form of a narrow elongated track, said radioactive material comprising a radioactive isotope which emits radiation, said apparatus comprising:

(a) first means for supporting a plurality of identical radiation detectors at a set of predetermined locations spaced along the length of the track, said radiation detectors being arranged in a straight line, said predetermined locations being equally spaced from one another, center to center, by a distance D, and each of said detectors producing an electrical output indicative of the amount of radioactive material in each said band in the vicinity of the detector;

(b) second means for receiving the medium containing the radioactive material;

(c) third means for moving the first and second means relative to one another in a step-like manner only along a path parallel to the straight line and parallel to the long axis of the track so as to position the medium and radioactive bands relative to the detectors at a plurality of predetermined positions which are equally spaced from one another by a distance d, the spacing D between the predetermined locations being several times greater than the spacing d between the predetermined positions, the total relative movement of the first and second means being equal to the spacing D between the predetermined locations; and (d) fourth means for simultaneously recording the electrical output of each of the detectors after each step at each of the predetermined positions.

6. The apparatus of claim 5 wherein the spacing between the predetermined location is greater than the spacing between the predetermined positions by a factor of 10 or more.

7. The apparatus of claim 5 wherein the first means is stationary and the second means is moved past the first means by the third means.

8. The apparatus of claim 5 wherein the radiation detectors are Geiger-Mueller detector tubes.

9. The apparatus of claim 8 wherein the first means includes identical collimating means for collimating the radiation emitted by the radioactive material in the medium before said radiation reaches the detectors each said collimating means forming a rectangular through in front of each of the detectors, the long axis of the rectangle extending across the width of the track so that each detector is primarily responsive to the transverse portion of the track nearest the detector rather than transverse portions of the track ahead or behind the nearest portion.

* * * * *